(12) United States Patent
Lavon et al.

(10) Patent No.: US 6,489,358 B2
(45) Date of Patent: Dec. 3, 2002

(54) PHARMACEUTICAL COMPOSITIONS CONTAINING MUPIROCIN

(75) Inventors: Ilana Lavon, Lehavim (IL); Amira Zeevi, Omer (IL); Stephen Cherkez, Ramat Gan (IL); Moshe Arkin, Kfar Shmaryahu (IL); Joseph Kaspi, Givatayim (IL); Chalil Abu-Gnim, Laqia (IL); Yoav Racchav, Be'er Sheva (IL)

(73) Assignee: Agis Industries (1983) Ltd., Bnei Brak (IL)

( * ) Notice: Subject to any disclaimer, the term of this patent is extended or adjusted under 35 U.S.C. 154(b) by 0 days.

(21) Appl. No.: 09/906,828

(22) Filed: Jul. 18, 2001

(65) Prior Publication Data

US 2002/0028843 A1 Mar. 7, 2002

(30) Foreign Application Priority Data

Jul. 18, 2000  (IS) .................................................. 137363

(51) Int. Cl.[7] .......................... A61K 31/35; A61K 9/06; A61K 47/00
(52) U.S. Cl. ........................ 514/460; 514/947; 424/405; 424/434
(58) Field of Search .................................. 514/460, 947; 424/405, 434

(56) References Cited

U.S. PATENT DOCUMENTS 4,873,012 A * 10/1989 Broze et al. ................. 510/304
6,156,792 A * 12/2000 Hatton et al. ............... 514/460

FOREIGN PATENT DOCUMENTS

EP            0 095 897      *  7/1983

OTHER PUBLICATIONS

Fernandez et al. A Double–blind, randomized, Placebo–controlled clinical trial to evaluate the safety and efficacy of mupirocin calcium ointment for eliminating nasal carriage of S.Aureus among hospital, J. of Antimicrob.Chemo.(1995) 35(3) pp. 399–408.*

* cited by examiner

Primary Examiner—Frederick Krass
Assistant Examiner—Donna Jagoe
(74) Attorney, Agent, or Firm—Banner & Witcoff, Ltd.

(57) ABSTRACT

The invention provides stable pharmaceutical preparations for topical and nasal uses, comprising Mupirocin calcium amorphous as an anti-microbial active agent therein, dissolved in a pharmaceutically acceptable solvent providing stability therefore.

8 Claims, No Drawings

PHARMACEUTICAL COMPOSITIONS CONTAINING MUPIROCIN

This application claims the benefit of Israeli Patent Application No. 137,363, which was filed on Jul. 18, 2000. The entire contents of this application are incorporated herein by reference.

The present invention relates to stable pharmaceutical and veterinary preparations for topical and nasal uses containing amorphous calcium mupirocin, also known as amorphous calcium pseudomonate as active ingredient therein.

Mupirocin is an antibiotic produced by aerobically culturing Pseudomonas Fluorescens. From the isolated Mupirocin, the calcium salt can be prepared.

Mupirocin and derivatives are mainly active against gram positive aerobes and some gram negative aerobes (Martindale p. 227, 32 ed., 1999). Mupirocin free acid, its salts and esters are described in UK patent # 1,395,907. These agents are found to be useful in treating skin, ear and eye disorders.

Currently, in the US market, there are three commercial products, which contain Mupirocin free acid or crystalline Mupirocin calcium dihydrate, as the active ingredients. These products are Bactroban® Ointment, Bactroban® Nasal and Bactroban® Cream, manufactured by SmithKline Beecham. The first contains Mupirocin, while the other two contain crystalline Mupirocin Calcium dihydrate.

The formulation of Bactroban® Ointment is protected under U.S Pat. No. 4,524,075. The formulation of Bactroban® Nasal is described in U.S Pat. No. 4,790,989. The cream base of Bactroban® Cream is described in world patent # 95/10999 and U.S Pat. No. 6,025,389.

Crystalline mupirocin calcium, its properties and methods of preparation are described in detail in U.S Pat. No. 4,916,155. This patent emphasizes on the improved thermal stability of the crystalline dihydrate form of the calcium salt. While at the same time, its poor solubility in water is mentioned as well. However, the poor solubility in water and in other hydrophilic solvents limits the formulation possibilities of this compound.

Furthermore, poor solubility of a drug substance in water may reduce its bioavailability within the body (Hancock and Zografi, J. Pharm. Sci., vol. 86, January 1997).

The dissolved state of the active ingredient within the formulation is preferred over the suspended form. In order to achieve a good clinical effect, the active ingredient has to reach the target area as soon as possible. This process involves two steps: dissolution and diffusion. By allowing the active substance to be dissolved within the formulation, we skip the first step of dissolution and obviate the second and hence, shorten the time it takes the active to reach the target area. In other words, keeping the active substance in a soluble state might increase the bioavailability. Thus a compound that will be both thermally stable and soluble in hydrophilic solvents will broaden the formulation scope of mupirocin.

Surprisingly, we found that unlike crystalline mupirocin calcium dihydrate, the amorphous compound is soluble in hydrophilic solvents. However, the different solubility profile, is not enough for formulation development because, as mentioned before, the amorphous material is claimed to be less thermally stable than the crystalline form.

We also found that we can overcome this stability problem by using a solution of the amorphous form in hexylene glycol. This solution was surprisingly found to be stable.

These findings enable us to formulate the amorphous forms of mupirocin calcium, for topical, nasal and other uses, in formulations such as creams, ointments, gels, solutions, sprays and other preparations not mentioned here.

Thus, according to the present invention, there is now provided stable pharmaceutical preparations for topical and nasal uses, comprising Mupirocin calcium amorphous as an anti-microbial active agent therein, dissolved in a pharmaceutically acceptable solvent providing stability therefore.

In preferred embodiments of the present invention, said Mupirocin calcium amorphous is dissolved in hexylene glycol.

In especially preferred embodiments of the present invention, said preparation comprises a hydrophilic phase consisting of Mupirocin calcium amorphous dissolved in Hexylene glycol, in admixture with one or more hydrophilic additives, dispersed in a hydrophobic phase, to create an essentially waterless cream.

In said embodiments, said hydrophilic additives are preferably selected from the group consisting of PEG 400, Propylene Carbonate, Butylene Glycol; and other pharmaceutically accepted additives.

In especially preferred embodiments, there is provided a cream preparation wherein the hydrophobic phase comprises an oleaginous base selected from the group consisting of petrolatum and hard fat; stiffening agents that are selected from the group consisting of cetostearyl alcohol, cetyl alcohol and stearyl alcohol; humectants selected from a group consisting of castor oil and oleyl alcohol; surfactants selected from the group consisting of a surfactant with an HLB equal to or below 5, and other pharmaceutically accepted additives.

The following table presents the solubility of mupirocin calcium amorphous, compared to the solubility of the crystalline form, in various pharmaceutically acceptable hydrophilic solvents. We prepared 2% solutions (calculated as free acid), similar to the commercially available products.

TABLE 1

| | Mupirocin Ca amorphous | | Mupirocin Ca crystalline | |
| --- | --- | --- | --- | --- |
| Solvent | Solubility (at room temperature) | Solubility (After heating for 30 min. at 70° C.) | Solubility (at room temperature) | Solubility (After heating for 30 min. at 70° C.) |
| Hexylene glycol | Soluble | Heating not necessary | Not soluble | Not soluble |
| Propylene glycol | Immediately soluble | Heating not necessary | Soluble | Heating not necessary |
| Glycerine | Not soluble | Soluble | Partially soluble | Partially soluble |
| Water | Immediately soluble | Heating not necessary | Not soluble | Not soluble |

The results show clearly the different behavior of the amorphous compound, compared with the crystalline one. The amorphous form is much more soluble in hydrophilic solvents. As mentioned above, this property provides us the opportunity to develop a wide range of pharmaceutical preparations for topical and nasal use, where the mupirocin calcium is in a dissolved state.

Mupirocin calcium amorphous is claimed to be less stable than the crystalline form. In order to be able to use the 2% solutions of Mupirocin calcium amorphous presented in the previous table, we have to ensure that the solutions are chemically stable.

The stability of Mupirocin Calcium amorphous in various acceptable pharmaceutical solvents was tested by heating a 2% solution to 80° C. for 24 hours or by heating it to 40° for 1 month. Bactroban cream was used as a reference. The results are presented in the following table:

TABLE 2

| Type of Solvent | Δ % impurities * (after heating for 24 h at 80° C.) | Δ % impurities * (after heating for 1 month at 40° C.) |
|---|---|---|
| Hexylene Glycol | 2 | 1.5 |
| Propylene Glycol | 8.7 | 7.5 |
| Glycerine | 29.4 | 29.2 |
| Water | 36.4 | 36.7 |
| Bactroban Cream | 29.6 | 5.4 |

* Δ % impurities = % impurities at time $t_1$ − % impurities at time $t_0$

It has to be noted that at 80° C. Bactroban Cream undergoes a phase separation. This explains the high percentage of impurities at 80° C. after 24 h.

The results presented in table 2, demonstrate the good stability of Mupirocin Calcium amorphous in Hexylene Glycol in absolute and relative terms. The stability of Mupirocin Calcium amorphous in Hexylene Glycol is not mentioned in the prior art. It is further to be noted from the data presented in Table 2 that Hexylene Glycol is a surprisingly preferred solvent, since mupirocin calcium amorphous decomposes to a significant amount in other similar pharmaceutically acceptable polyols.

The discovery of the stable solution of Mupirocin calcium amorphous in Hexylene Glycol provides us several possibilities for pharmaceutical preparations, such as ointments, creams, lotions, solutions and other topical preparations which are not mentioned herein. The invention is demonstrated but not limited to, in the following examples. Usually the mupirocin calcium amorphous is first dissolved in hexylene glycol and then mixed with the other ingredients.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Example # 1

Ointment Formulation

| Ingredients | % w/w |
|---|---|
| Hard Fat | 85.85 |
| Hexylene Glycol | 12 |
| Mupirocin Calcium amorphous | 2.15 (equivalent to 2% Mupirocin free acid) |

Example # 2

Ointment Formulation

| Ingredients | % w/w |
|---|---|
| Hard Fat | 77.85 |
| Propylene Glycol Stearate | 8 |
| Hexylene Glycol | 12 |
| Mupirocin Calcium amorphous | 2.15 (equivalent to 2% Mupirocin free acid) |

Example # 3

Waterless Cream Formulation

| Ingredients | % w/w |
|---|---|
| White petrolatum | 25.85 |
| Mineral oil | 13 |
| Lanoline alcohol | 8 |
| Cetostearyl alcohol | 15 |
| Aluminum stearate | 3 |
| PEG 400 | 20 |
| Titanium dioxide | 1 |
| Hexylene Glycol | 12 |
| Mupirocin Calcium amorphous | 2.15 (equivalent to 2% Mupirocin free acid) |

Example # 4

Solution Formulation

| Ingredients | % w/w |
|---|---|
| PEG 400 | 85.85 |
| Hexylene Glycol | 12 |
| Mupirocin Calcium amorphous | 2.15 (equivalent to 2% Mupirocin free acid) |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A stable pharmaceutical preparation for topical and nasal uses, comprising Mupirocin calcium amorphous as an anti-microbial active agent therein, in combination with a pharmaceutically acceptable solvent providing stability therefor.

2. A preparation, according to claim 1, wherein Mupirocin calcium amorphous is dissolved in hexylene glycol.

3. An ointment preparation, according to claim 2, where Mupirocin calcium amorphous is dissolved in hexylene glycol and dispersed in an oleaginous base, selected from a group consisting of white petrolatum and hard fat and a suitable emulsifier.

4. A preparation according to claim 3, where said emulsifier is propylene glycol monostearate.

5. An ointment preparation, according to claim 3, comprising:

| | |
|---|---|
| Hard fat | 77.85% |
| Propylene glycol monostearate | 8% |
| Hexylene glycol | 12% |
| Mupirocin calcium amorphous | 2.15 (equivalent to 2% Mupirocin free acid). |

6. A preparation according to claim 1, comprising a hydrophilic phase consisting of Mupirocin calcium amorphous dissolved in Hexylene glycol, in admixture with one or more hydrophilic additives, dispersed in a hydrophobic phase.

7. A preparation, according to claim 6, wherein the hydrophilic additives are selected from a group consisting of PEG 400, Propylene Carbonate, Butylene Glycol; and other pharmaceutically accepted additives.

8. A cream preparation according to claim 6, where the hydrophobic phase comprises an oleaginous base selected from the group consisting of petrolatum and hard fat; stiffening agents that are selected from the group consisting of cetostearyl alcohol, cetyl alcohol and stearyl alcohol; humectants selected from a group consisting of castor oil and oleyl alcohol; surfactants selected from the group consisting of a surfactant with an HLB equal to or below 5, and other pharmaceutically accepted additives.

* * * * *

UNITED STATES PATENT AND TRADEMARK OFFICE
CERTIFICATE OF CORRECTION

PATENT NO. : 6,489,358 B2
DATED : December 3, 2002
INVENTOR(S) : Ilana Lavon et al.

It is certified that error appears in the above-identified patent and that said Letters Patent is hereby corrected as shown below:

<u>Title page,</u>
Item [75], Inventors, "Racchav" has been replaced with -- Raechav --, <u>Column 4,</u>
Line 60, "therefor" has been replaced with -- therefore --.

Signed and Sealed this

Twenty-sixth Day of August, 2003

JAMES E. ROGAN
*Director of the United States Patent and Trademark Office*